(12) United States Patent
Ness et al.

(10) Patent No.: US 6,444,422 B2
(45) Date of Patent: *Sep. 3, 2002

(54) COMPUTER METHOD AND SYSTEM FOR CORRELATING DATA

(75) Inventors: Jeffrey Van Ness, Seattle; John C. Tabone, Bothell; J. Jeffry Howbert, Bellevue; John T. Mulligan, Seattle, all of WA (US)

(73) Assignee: Qiagen Genomics, Inc., Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/120,686

(22) Filed: Jul. 21, 1998

Related U.S. Application Data

(60) Provisional application No. 60/053,429, filed on Jul. 22, 1997.

(51) Int. Cl.⁷ .................................................. C12Q 1/68
(52) U.S. Cl. ........................ 435/6; 435/71.1; 435/287.2; 435/288.7; 436/173; 536/25.3; 536/25.4; 935/77; 935/78; 702/20; 703/11
(58) Field of Search ........................ 435/6, 71.1, 287.2, 435/288.7; 436/173; 536/25.3, 25.4; 935/77, 78; 703/11; 702/20

(56) References Cited

U.S. PATENT DOCUMENTS

| | | | |
|---|---|---|---|
| 4,020,698 A | 5/1977 | D'Autry | 73/425.6 |
| 4,827,780 A | 5/1989 | Sarrine et al. | 73/864.21 |
| 4,981,783 A | 1/1991 | Augenlicht | 435/6 |
| 5,143,854 A | 9/1992 | Pirrung et al. | 436/518 |
| 5,384,261 A | 1/1995 | Winkler et al. | 436/518 |
| 5,436,327 A | 7/1995 | Southern et al. | 536/25.34 |
| 5,474,796 A | 12/1995 | Brennan | 427/2.13 |
| 5,525,464 A | 6/1996 | Drmanac et al. | 435/6 |
| 5,547,835 A * | 8/1996 | Koster | 435/6 |
| 5,658,802 A | 8/1997 | Hayes et al. | 436/518 |
| 5,709,668 A | 1/1998 | Wacks | 604/232 |
| 5,741,554 A | 4/1998 | Tisone | 427/424 |
| 5,744,305 A | 4/1998 | Fodor et al. | |
| 5,770,151 A | 6/1998 | Roach et al. | 422/63 |
| 5,770,367 A | 6/1998 | Southern et al. | 435/6 |
| 5,800,992 A | 9/1998 | Fodor et al. | 435/6 |
| 5,807,522 A | 9/1998 | Brown et al. | 422/50 |
| 6,101,946 A | 8/2000 | Martinsky | 101/494 |

FOREIGN PATENT DOCUMENTS

| | | |
|---|---|---|
| EP | 221 308 B1 | 5/1987 |
| WO | WO 92/03579 | 3/1992 |
| WO | WO 92/13629 | 8/1992 |
| WO | WO 94/00600 | 1/1994 |
| WO | WO 94/16101 | 7/1994 |
| WO | WO 95/04160 | 2/1995 |
| WO | WO 97/27331 | 7/1997 |

OTHER PUBLICATIONS

Blanchard et al., (1996), "High–density oligonucleoyide arrays," *Biosens. Biolectron.* 11:687–690.

Chee et al., (1996), "Accessing genetic information with high–density DNA arrays," *Science* 274: 610–614.

Chu et al., (1998), "The transcriptional program of sporulation in budding yeast," *Science* 282, 699–705.

Cronin et al., (1996), "Cystic Fibrosis Mutation Detection by Hybridization to Light–Generated DNA Probe Arrays,"*Human Mutation* 7:244–245.

DeRisi et al., (1996), "Use of a cDNA microarray to analyze gene expression patterns in human cancer," *Nat Genet* 14: 457–460.

DeRisi et al., (1997), "Exploring the metabolic and genetic control of gene expression on a genomic scale," *Science* 278: 680–686.

de Saizieu et al., (1998), "Bacterial transcript imaging by hybridization of total RNA to oligonucleotide arrays," *Nature Biotech.* 16: 45–48.

Drmanac et al., (1998), "Accurate sequencing by hybridization for DNA diagnostics and individual genomics," *Nature Biotech.* 16: 54–58.

Fodor et al. (1991), "Light–directed, spatially addressable parallel chemical synthesis," *Science* 251: 767–773.

Hacia et al., (1996), "Detection of heterozygous mutations in BRCA1 using high density oligonucleotide arrays and two–colour fluorescence analysis," *Nature Genet.* 14: 441–447.

Heller et al., (1997), "Discovery and analysis of inflammatory disease–related genes using cDNA microarrays," *Proc Natl Acad Sci USA.* 94: 2150–2155.

Khrapko et al., (1991), "Hybridization of DNA with oligonucleotides immobilized in gel: a convenient method for detecting single base substitutions," *Molecular Biology* 25: 581–591.

Kozal et al., (1996), "Extensive polymorphisms observed in HIV–1 clade B protease gene using high–density oligonucleotide arrays," *Nature Med.* 2: 753–759.

(List continued on next page.)

Primary Examiner—W. Gary Jones
Assistant Examiner—Janell E. Taylor
(74) Attorney, Agent, or Firm—SEED Intellectual Property Law Group PLLC

(57) ABSTRACT

A method and system for correlating characteristics (e.g., type of nucleotide) of biomolecules (e.g., DNA) to molecular tags with unique molecular weights that are associated with the biomolecule. In one embodiment. the molecular tags are applied to primers used when synthesizing the biomolecule. The system initially receives a mapping of each characteristic of the biomolecules to the corresponding molecular weight of the molecular tag. The system also receives an indication of the molecular weights detected when analyzing the biomolecules to which the molecular tags have been associated. For each molecular weight detected, the system determines based on the received mapping the characteristic corresponding to the detected molecular weight. The system then indicates that the analyzed biomolecule has the determined characteristic.

19 Claims, 7 Drawing Sheets

OTHER PUBLICATIONS

Lashkari et al., (1997), "Yeast microarrays for genome wide parallel genetic and gene expression analysis," *Proc. Natl. Acad. Sci. USA 94*: 13057–13062.

Lemieux et al., (1998) "Overview of DNA Chip Technology," *Molecular Breeding 4*: 277–289.

Lockhart et al., (1996), "Expression Monitoring by Hybridization to High–Density Oligonucleotide Arrays," *Nature Biotechnology 14*: 1675–1680.

Maier et al., (1994), "Application of robotic technology to automated sequence fingerprint analysis by oligonucleotide hybridisation," Summary.

Pease et al., (1994), "Light–generated oligonucleotide arrays for rapid DNA sequence analysis," *Proc. Natl. Acad. Sci. USA 91*: 5022–5026.

Sapolsky and Lipshutz, (1996), "Mapping Genomic Library Clones Using Oligonucleotide Arrays," *Genomics 33*: 445–456.

Schena et al., (1995), "Quantitative monitoring of gene expression patterns with a complementary DNA microarray," *Science 270*: 467–470.

Schena, M., (1996), "Genome Analysis with Gene Expression Microarrays," *BioEssays 18*: 427–431.

Schena et al., (1996), "Parallel human genome analysis: microarray–based expression monitoring of 1000 gene," *Proc Natl Acad Sci USA 93*: 10614–10619.

Schena et al., (1998), "Microarrays: Biotechnology's discovery platform for functional genomics," *Trends Biotech. 16*: 301–306.

Schena and Davis, (1998), "Parallel Analysis with Biological Chips. in PCR Methods Manual," Academic Press (San Diego), in press.

Shalon et al., (1996), "A DNA micro–array system for analyzing complex DNA samples using two–color fluorescent probe hybridization," *Genome Research 6*: 639–645.

Shoemaker et al., (1996), "Quantitative phenotypic analysis of yeast deletion mutants using a highly parallel molecular bar–coding strategy," *Nature Genetics 14*: 450–456.

Wodicka et al., (1997), "Genome–wide expression monitoring in *Saccharomyces cerevisiae*," *Nature Biotech. 15*: 1359–1367.

Yershov et al. (1996), "DNA analysis and diagnostics on olignonucleotide microchips," *Proc. Natl. Acad. Sci. USA 93*: 4913–4918.

http://cmgm.stanford.edu/pbrown/mguide, Sep. 12, 2000 and http://cmgm.stanford.edu/pbrown/mguide/tips.html, Sep. 12, 2000.

Van Ness et al., "A versatile solid support system for oligodeoxynucleotide probe–based hybridization assays," *Nucleic Acids Research 19*(12): 3345–3350, 1991.

* cited by examiner

MW Table

| MW | Time 1 | 2 | 3 | 4 | . . . | 1999 | 2000 |
|---|---|---|---|---|---|---|---|
| 110 | | | 50 | | | | |
| 120 | | | 0 | | | | |
| 130 | | | 0 | | | | |
| ⋮ | ⋮ | ⋮ | ⋮ | ⋮ | ⋮ | ⋮ | ⋮ |
| 520 | | | 200 | | | | |
| 530 | | | 5 | | | | |

*Fig. 3*

COMPUTER METHOD AND SYSTEM FOR CORRELATING DATA

CROSS-REFERENCE TO RELATED APPLICATION

The present application claims the benefit of U.S. Provisional Patent Application No. 60/053,429, filed Jul. 22, 1997.

TECHNICAL FIELD

The present invention relates generally to a computer system and method for correlating data, and more particularly, to correlating tagged data to information associated with the tagged data.

BACKGROUND OF THE INVENTION

The identification of the sequence of bases which constitute an oligonucleotide (ODN) is commonly performed by Sanger sequencing, which is named after Dr. Fred Sanger who introduced the sequencing in 1976. As currently practiced, Sanger sequencing employs radioactively labeled molecules to determine the sequence of a sample oligonucleotide. The radioactivity labeled molecules are used in the enzymatic synthesis of radioactively labeled oligonucleotide fragments. The fragments have base sequences that are identical to the sequence of the sample oligonucleotide. In order to determine the sequence of the sample oligonucleotide, the radioactive fragments generated by Sanger sequencing are separated using gel electrophoresis. Gel electrophoresis creates a two-dimensional map that, upon analysis, yields information about the base sequence of the sample oligonucleotide.

Although Sanger sequencing is used in laboratories around the world, it has significant shortcomings. One shortcoming is that the two-dimensional gel electrophoresis map is processed by analyzing the radioactivity of the fragments. Radioactive materials raise health concerns for many people who work in this area. Another shortcoming is that gel electrophoresis only provides maps of limited size. In particular, it is very difficult to create a single map that provides sequence information for an oligonucleotide formed from more than about 1,000 bases. Yet another shortcoming is that it is very difficult to automate the analysis of the two-dimensional gel electrophoresis map.

A current approach, which partially overcomes these shortcomings, is the use of fluorescently labeled molecules, rather than radioactively labeled molecules to create the fragments. As commonly practiced, four unique labels corresponding to each unique base (i.e., A, T, C, and G) are used. This use of fluorescently labeled molecules allows column chromatography, rather than gel electrophoresis, to be used to separate the labeled fragments. Column chromatography is typically a more efficient technique than gel electrophoresis for separating fragments and is more amenable to automation than gel electrophoresis. Despite the avoidance of radioactivity and the efficiency of the separation, the use of fluorescently labeled molecules in conjunction with Sanger sequencing is not widespread. The primary problem with the use of fluorescent labels with Sanger sequencing is that only a few fluorescent labels can be detected in a single assay (always less than 8, usually only 4), which limits the DNA sequencing throughput to one or two samples per lane or per column. Currently, devices using fluorescent labeling are commercially available that can automatically sequence fragments. These devices, however, are rather expensive and still have this primary problem.

Accordingly, there is a need in the art for improved approaches to the basic Sanger sequencing. Preferably, the improved approach would avoid the use of radioactively labeled molecules, be amenable to automation, utilize equipment that is commonly available in research and development laboratories, be highly accurate even for long oligonucleotide sequences, and be efficient in allowing for many oligonucleotide samples to be analyzed simultaneously.

SUMMARY OF THE INVENTION

The present invention provides a method and system for correlating characteristics (e.g., type of nucleotide) of biomolecules (e.g., DNA) to molecular tags with unique molecular weights that are associated with the biomolecule. In one embodiment, the molecular tags are applied to primers used when synthesizing the biomolecule. The system initially receives a mapping of each characteristic of the biomolecules to the corresponding molecular weight of the molecular tag. The system also receives an indication of the molecular weights detected when analyzing the biomolecules to which the molecular tags have been associated. For each molecular weight detected, the system determines based on the received mapping the characteristic corresponding to the detected molecular weight. The system then indicates that the analyzed biomolecule has the determined characteristic.

BRIEF DESCRIPTION OF THE DRAWINGS

FIG. 3 is a diagram illustrating the output of the mass spectrometer.

DETAILED DESCRIPTION OF THE INVENTION

Figure 1:
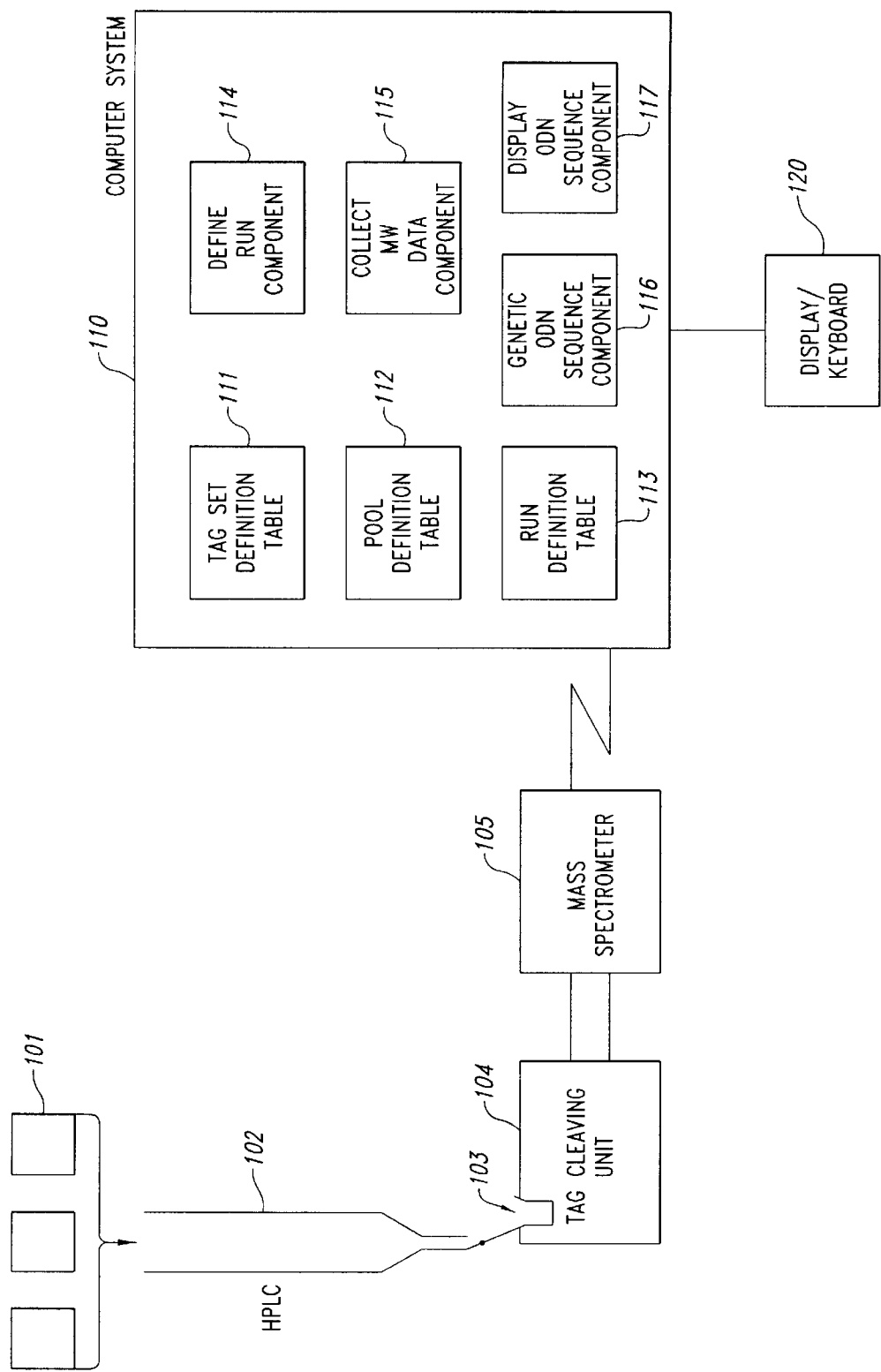
FIG. 1 is a block diagram illustrating the components of a nucleotide sequencing system.

The present invention provides a computer-based method and system for analyzing biomolecules by applying molecular tags to the biomolecules, by detecting attributes of the molecular tags, and by using those attributes to identify characteristics of the biomolecules themselves. The biomolecular characteristic identification ("BCID") system of the present invention receives a mapping of the attributes of the molecular tags to corresponding characteristics of the biomolecules. The molecular tags are then applied to the biomolecules. The tagged biomolecules are then analyzed by measuring the attributes of the molecular tags. The BCID system uses these measured attributes and the mapping to identify characteristics of the biomolecules.

In one embodiment, the attribute of the molecular tags is molecular weight. Each molecular tag has unique molecular weight so it can be uniquely identified. The tagged biomolecules are analyzed by a mass spectrometer to identify the molecular weight of the molecular tag that has been applied to the biomolecule. The characteristic of the biomolecule is then identified from the molecular tag. The tagged biomolecules can be preprocessed prior to analysis by the mass spectrometer so that other characteristics of the tagged biomolecules can be derived. For example, the tagged biomolecules can be eluted through a packed column so that the tagged biomolecules exit the packed column in an order that is based on the length of the tagged biomolecules. That is, shorter biomolecules exit the packed column first. Thus, the mass spectrometer analyzes shorter tagged biomolecules first. The BCID system uses the mapping of molecular weights to characteristics and information resulting from the preprocessing to identify characteristics of the biomolecules.

The BCID system can be used to identify characteristics of biomolecules in many different assays and procedures. In the following, the BCID system is described as it is used to identify the base sequences of oligonucleotides, including DNA fragments of any length (nucleotide sequencing), to determine whether the base sequences of two oligonucleotides are different (mutation detection), and to compare the genes that are expressed in biological samples (differential display).

Nucleotide Sequencing

Nucleotide sequencing is the process of identifying the sequence of bases in an oligonucleotide ("ODN") whose sequence is unknown. The first step in nucleotide sequencing is to obtaining an ODN sample with an unknown sequence (the "original ODN"). For example, the original ODN may have the sequence TAGCATTAGCTGCC, which is currently unknown. The second step in nucleotide sequencing is to produce many ODNs (the "complementary ODNs") from the original ODN. These complementary ODNs all have the same (also unknown) sequence, but that sequence is the reverse complement of the sequence of the original ODN. For example, the complementary sequence of the original sequence is GGCAGCTAATGCTA. The third step of nucleotide sequencing is to divide these complementary ODNs into four portions, that is, one portion for each base (i.e., A, T, C, and G) and place each portion into a separate container. Each of the four containers contains a set of synthesizing biomolecules which, when mixed with the complementary ODN, synthesize ODNs having a sequence which is complementary to the sequence of the complementary ODNs and thus identical to the sequence of the original ODN. For example, the synthesized ODNs have the sequence TAGCATTAGCTGCC, which is identical to the sequence of the original ODN. These synthesizing biomolecules include an enzyme and the four building blocks (i.e., dATP, dTTP, dCTP, and dGTP) used in enzymatic synthesis. A "primer" sequence is used by the enzyme to start the synthesis of the building blocks into the synthesized ODNs.

At this point, each of the four containers contain the identical components: the complementary ODNs and the synthesizing biomolecules. However, the fourth step of the nucleotide sequencing adds a unique molecular tag to each container. To the first container is added ddATP, which is the dideoxy analog of dATP, and a primer with a molecular tag that has a unique molecular weight ($MW_1$). The enzyme will incorporate the ddATP ("A*") into the synthesized ODNs in competition with the incorporation of dATP ("A") into the synthesized ODN. However, ddATP and dATP are functionally different in that after ddATP has been incorporated into the synthesized ODN, the enzyme is unable to incorporate any additional bases into that particular ODN. For example, if the fully synthesized ODN would have the sequence TAGCATTAGCTGCC, the enzyme synthesizes this sequence by adding from left to right to the primer sequence (i.e., beginning by adding a T to the primer to provide primerT, by adding an A to the primerT to provide primerTA, by adding a G to the primerTA to provide primerTAG, and so on). The enzyme will in some instances add ddATP, rather than dATP, to the primerT to provide primerTA*. The enzyme will be unable to continue the sequence because A* effectively stops the enzyme from adding the next base. However, in other instances, the enzyme will add dATP ("A") to the primerT sequence to provide the sequence primerTA. The enzyme will then proceed with the adding of G and C to provide primerTAGC. However, at this point, when the enzyme proceeds to add an A to primerTAGC, either A or A* may be added. If A* is added, then primerTAGCA* is produced, and the enzyme is unable to add any further bases to this sequence. If A is added, then primerTAGCA is produced, and the enzyme may continue adding bases, until primerTAGCATT is produced. At this point, again either A or A* may be added.

After the enzyme has had sufficient time to act in the first container, there will be synthesized four kinds of ODNs, distinguished by having the following sequences: primerTAGCATTAGCTGCC, primerTAGCATTA*, primerTAGCA*, and primerTA*. Since all of the ddATP molecules are associated with a primer that carries a molecular tag with a molecular weight $MW_1$, every synthesized ODN having less than the complete sequence of 14 bases will contain the molecular tag with the molecular weight $MW_1$. More specifically, the molecular tag with the molecular weight $MW_1$ will be found on the synthesized ODNs that are 2, 5, and 8 bases long (not counting the primer sequence, which has a constant length).

To the second container is added ddTTP, which is the dideoxy analog of dTTP. The added ddTTP functions with respect to dTTP in an analogous way as ddATP functions with respect to dATP. The added ddTTP molecules are associated with a primer that carries a molecular tag that has a unique molecular weight ($MW_2$). Therefore, in the second container, there will be synthesized the sequences: primerTAGCATTAGCTGCC, primerTAGCATTAGCT*, primerTAGCATT*, primerTAGCAT*, and primerT*. Accordingly, the molecular tag with the molecular weight $MW_2$ will be found on the synthesized ODNs that are 1, 6, 7, and 11 bases long.

In a like manner, to the third container is added ddCTP, which is the dideoxy analog of dCTP. The added ddCTP molecules are associated with a primer that carries a molecular tag that has a unique molecular weight ($MW_3$). Therefore, in third container there will be synthesized the sequences: primerTAGCATTAGCTGCC*, primerTAGCATTAGCTGC*, primerTAGCATTAGC*, and primerTAGC*. The molecular tag with the molecular weight $MW_3$ will be found on the synthesized ODNs that are 4, 10, 13, and 14 bases long. To the fourth container is added ddGTP, which is the dideoxy analog of dGTP. The added ddGTP molecules are associated with a primer that carries a molecular tag that has a unique molecular weight ($MW_4$). Thus, in the fourth container there will be synthesized sequences: primerTAGCATTAGCTG*, primerTAGCATTAG*, and primerTAG*. The molecular tag with the molecular weight $MW_4$ will be found on the synthesized ODNs that are 3, 9, and 12 bases long.

The fifth step of nucleotide sequencing is to combine the contents of the four containers and elute the combined contents through a packed column using high-pressure liquid chromatography (HPLC). The result is that the synthesized ODNs are separated on the basis of size, with the shorter synthesized ODNs eluting through the packed column first. Thus, the first synthesized ODN to elute through the column will be primerT*, the next will be primerTA*, followed by primerTAG*, etc.

The sixth step of nucleotide sequencing is to process the output (i.e., eluent) of the packed column with a tag cleaving unit coupled to a mass spectrometer. Accordingly, when primerT* comes off the column, the molecular tag is released and the mass spectrometer records the presence of molecular weight $MW_2$, because ddTTP (T*) is associated with a primer that carries a molecular tag with the molecular weight $MW_2$. Likewise, when primerTA* comes off the column, the mass spectrometer records the presence of molecular weight $MW_1$, because ddATP is associated with a primer that carries a molecular tag with a molecular weight $MW_1$. Thus, the mass spectrometer will thus record, in order, molecular weights $MW_2$, $MW_1$, $MW_4$, $MW_3$, $MW_1$, $MW_2$, $MW_2$, $MW_1$, $MW_4$, $MW_3$, $MW_2$, $MW_4$, $MW_3$ and $MW_3$.

The BCID system can then use a previously specified mapping of the molecular tags to the bases to identify the sequence of the original ODN. The BCID system receives each molecular weight and determines the corresponding base. Because the synthesized ODNs were preprocessed through the packed column, the order of the recorded molecular weights corresponds to the order of the bases in the original ODN. The BCID system outputs the sequence of the determined bases as the nucleotide sequence for the original ODN.

The nucleotide sequencing using molecular tags with unique molecular weights can be used to simultaneously identify the sequence of multiple sample ODNs with unknown sequences. Each sample ODN has its own set of four separate containers. The same steps as the first four steps for a single sample ODN are performed for each of the multiple sample ODNs. In particular, the complementary ODNs of each sample ODN are placed into four separate containers. Each container contains the enzyme and the building blocks. Each container in a set of four containers for a sample ODN contains one of the four dideoxy analogs. However, each dideoxy analog is associated with a primer that carries a molecular tag with a molecular weight that is unique among all of the containers for all the sample ODNs. For example, a container for the first sample ODN may contain ddATP, which is associated with a primer that carries a molecular tag that has a molecular weight of $MW_1$, and a container for the second sample may contain ddATP, which is associated with a primer that carries a molecular tag that has a molecular weight of $MW_5$. In the fifth step of nucleotide sequencing, rather than combining only the contents of the four containers for the single sample ODN, the contents of all the containers for all samples are combined. The combined contents are then eluted through the packed column. As a result of combining the contents for multiple samples, there will be one sequence of each length for each sample ODN. Since multiple synthesized ODNs have the same length, the synthesized ODNs of the same length will elute through the packed column at the same time and enter the mass spectrometer at the same time. For example, if two sample ODNs have been synthesized and their combined contents eluted through the packed column, then the synthesized ODNs of length 1 will exit the column at the same time. If the dideoxy analog for the first base of the first sample ODN has a molecular tag with a molecular weight of $MW_2$ and the dideoxy analog for the first base of the second sample ODN has a molecular tag with a molecular weight of $MW_5$, then the mass spectrometer will report the simultaneous presence of molecular weight $MW_2$ and molecular weight $MW_5$.

The BCID system contains a mapping of each molecular tag with a unique molecular weight to the sample ODN and the base to which it is assigned. Using this mapping, the BCID system may determine, for example, that the first base in the sequence for the first sample ODN is T and that the first base in the sequence for the second sample ODN is A. The BCID repeats this process for each of the molecular weights that are detected by the mass spectrometer to simultaneously identify the sequence for each of the sample ODNs.

FIG. 1 is a block diagram illustrating the components of a nucleotide sequencing system. The nucleotide sequencing system includes containers 101, packed column 102, tag cleaving unit 104, mass spectrometer 105, and the BCID system 110. The containers 101 are filled with the synthesized ODNs to be eluted through the packed column 102. The output of the packed column is shunted via shunt 103 to the tag cleaving unit 104. The output of the tag cleaving unit is then input to the mass spectrometer 105. The output of the mass spectrometer is then input into the BCID system 110. The tag cleaving unit separates the molecular tags from the synthesized ODN. These molecular tags are then sent to the mass spectrometer to have their molecular weight analyzed. The BCID system 110 comprises various data structures 111–113 and various functional components 114–117. The tag set definition table 111 contains the identification of the molecular weights of each set of four molecular tags that is used to identify the bases of a sample ODN. A set of molecular tags is defined for each sample ODN whose synthesized ODN is combined (pooled) and eluted through the packed column simultaneously. The pool definition table 112 identifies the sets of tags that are assigned to each sample ODN in a pool. The run definition table 113 contains a list of all the sample pools that are to be run through the nucleotide sequencing system serially. The define run component 114 provides the user with an interface through which to define each of the pools and the sets of molecular tags to be used with each sample ODN in a pool. The defined run component also allows the user to identify the pools that are scheduled to be run through the nucleotide sequencing system serially. The collect molecular weight data component 115 receives the data generated by the mass spectrometer and identifies the various peaks within the data. These peaks indicate that a molecular tag with a certain molecular weight was detected during a certain time interval. The generate ODN sequence component 116 uses the tables 111–113 to map the molecular weights detected by the mass spectrometer to the sequences corresponding to those molecular weights. The display ODN sequence component 117 displays a graph of the molecular weights and the corresponding sequences. The display ODN sequence component allows the user to make modifications to the identified sequence to correct any errors resulting from in the automated sequencing. The components and data structures of the tables of the BCID system may be stored persistently on a computer-readable medium, such as a CD-ROM, and downloaded into memory of the computer system to perform the processing of the BCID system.

Figure 2:
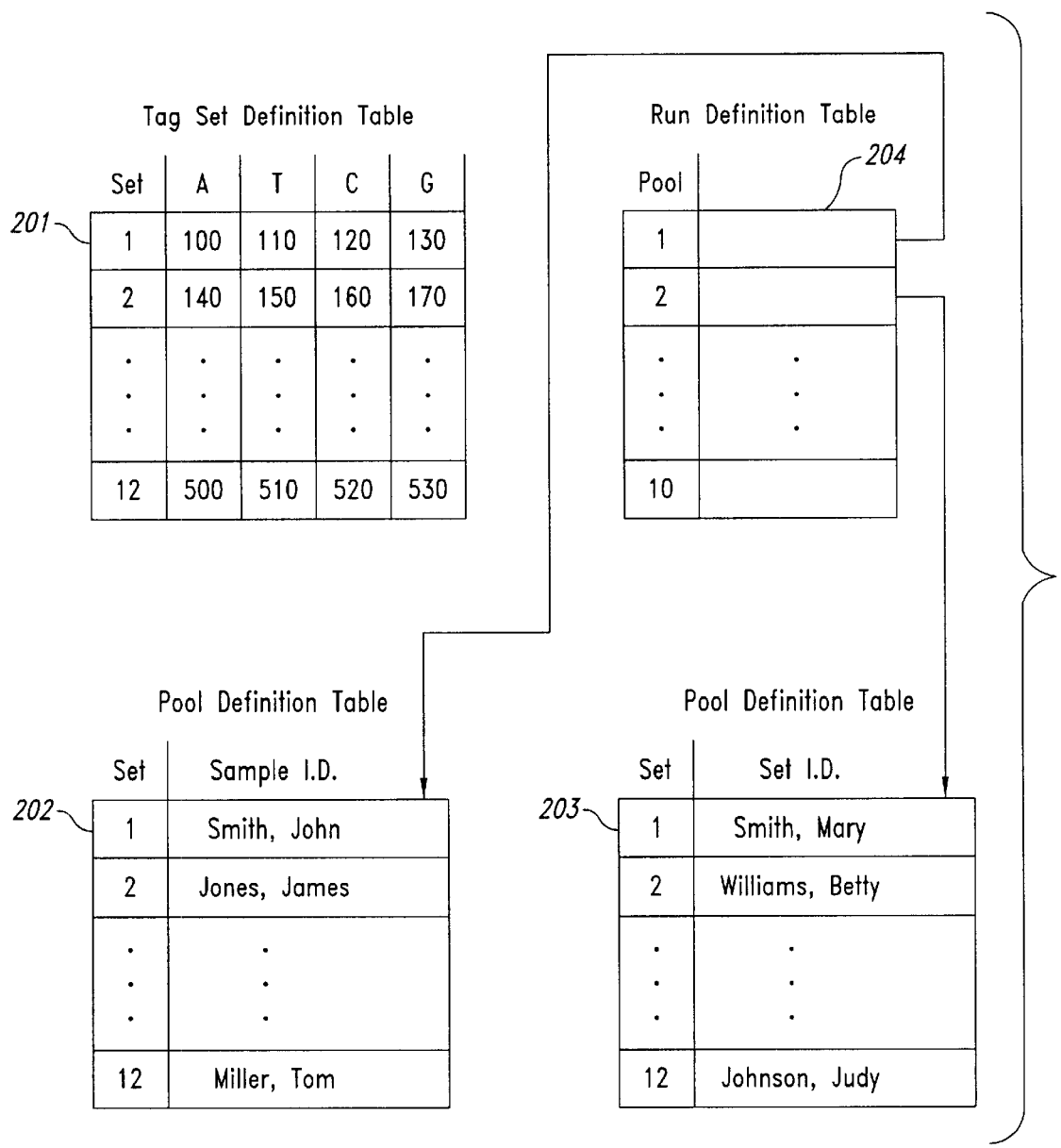
FIG. 2 is a diagram illustrating the tables used by the BCID system.

FIG. 2 is a diagram illustrating the tables used by the BCID system. The tag set definition table 201 contains a row for each of the twelve samples that can be combined into a single pool and processed by the nucleotide sequencing system simultaneously. The tag set definition table is preferably pre-loaded by the developers of the BCID system. This table is pre-loaded with the sets of the molecular weights of the molecular tags that are provided with the nucleotide sequencing system. Each row of the table identifies one set of molecular tags. Each set contains four unique molecular tags for the four bases (i.e., A, T, C, and G). The tag set definition table 201 contains sample data. The first row of the tag set definition table corresponds to the first set and indicates that the molecular weights of the molecular tags in the set are 100, 110, 120, and 130 corresponding to tags to bases A, T, C, and G. respectively. Each of the molecular weights in the tag set definition table are unique so that each base for each sample can be uniquely identified. The pool definition tables 202 and 203 contain a correlation between the tag sets and the sample ID for each sample ODN to be combined in a single pool. As shown in table 202, the sample ID corresponding to John Smith has been assigned the tag set number 1, which are the molecular tags with molecular weights of 100, 110, 120, and 130. The user of the nucleotide sequencing system inputs the information to the BCID system to indicate which tag sets have been assigned to which samples ODNs. The user of the BCID system can define various pools of samples. Each pool has its own pool definition table. The run definition table 204 lists the various pools that are to be serially processed by the nucleotide sequencing system. Each row of the run definition table contains an identification of the pool number and a reference to the pool definition table.

FIG. 3 is a diagram illustrating the output of the mass spectrometer. The mass spectrometer periodically samples the molecular weights being supplied by the tag cleaving unit. For example, the mass spectrometer may sample the molecular weights 100 times a minute. Each time the mass spectrometer samples the molecular weights, it stores the number of molecules detected for each molecular weight in the molecular weight table. For example, as shown in time interval three, the mass spectrometer detected that there were 50 molecules with a molecular weight of 110, no molecules with a molecular weight of 120 or 130, 200 molecules with a molecular weight of 520, and 5 molecules with a molecular weight of 530.

Figure 4:
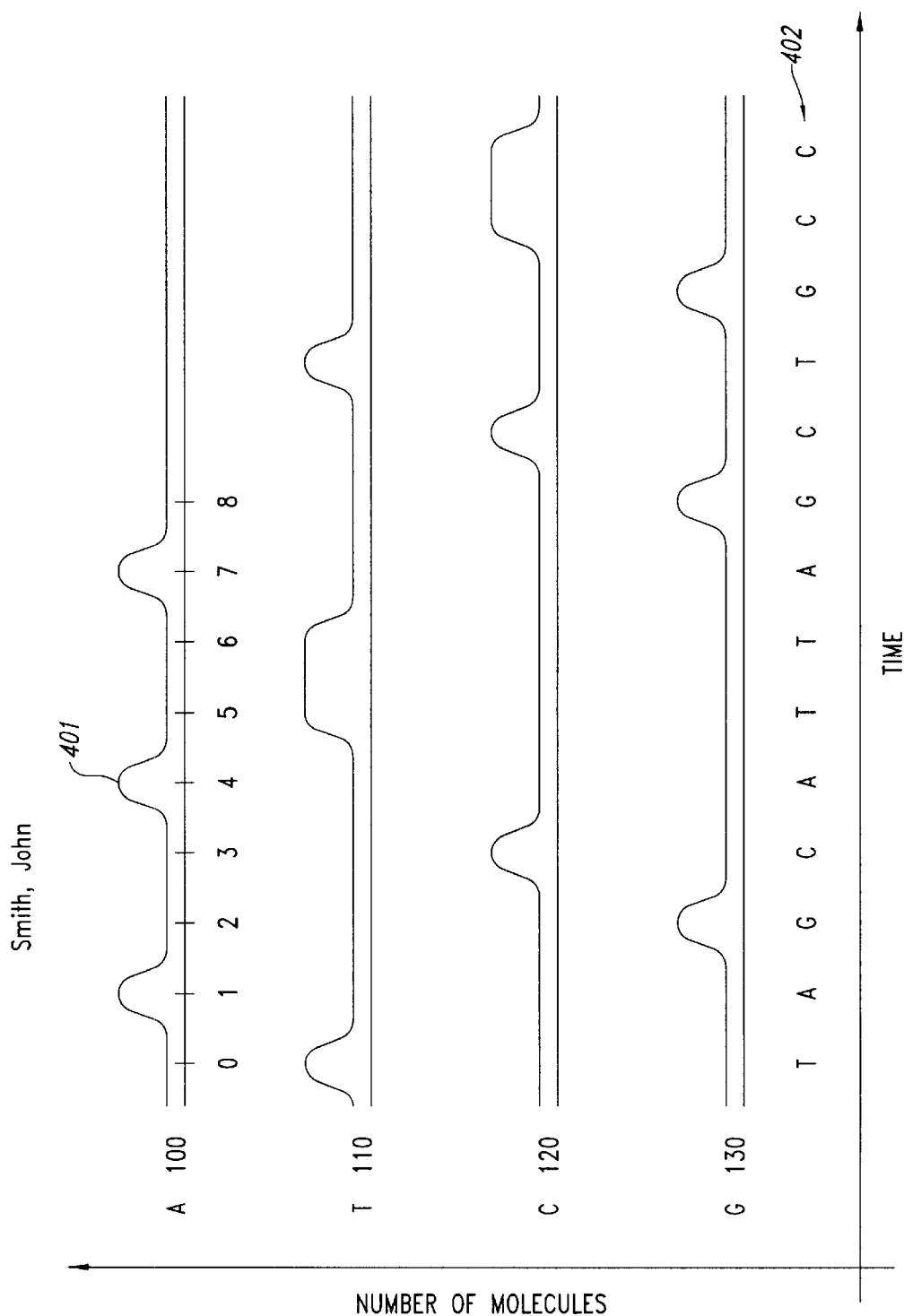
FIG. 4 contains a graph illustrating the number of molecules detected for various molecular weights at various time intervals for molecular weights 110, 120, 130, and 140.

FIG. 4 contains a graph illustrating the number of molecules detected at various time intervals for molecular weights 110, 120, 130, and 140. The horizontal axis of the graphs represents time, and the vertical axis represents the number of molecules. Each peak on the graph indicates that a particular synthesized ODN with a particular length eluted through the packed column at that time. For example, the peak 401 indicates that the mass spectrometer detected many molecules at time 4 with a molecular weight of 100. The collect molecular weight data component analyzes the molecular weight table to identify the various peaks. For a given tag set of molecular weights, only one peak for one of the molecular weights should be detected at a time. Various filtering techniques may be used to detect the peaks in the molecular weight table. Once the peaks are detected, then the generate ODN sequence component processes the information for each tag set of molecular weights to determine the sequence. The BCID system first identifies the molecular weight associated with the first peak for a sample ODN. The BCID system then retrieves from the tag set definition table the particular base that is associated with that molecular weight. The BCID system outputs that particular base as the first base in the sequence of that sample ODN. The BCID system then identifies the molecular weight associated with the second peak for that sample ODN. The BCID system determines the base associated with that molecular weight and outputs that as the second base in the sequence of that sample ODN. The BCID system repeats this process for all the peaks and for all the sample ODNs. Sequence 402 illustrates the base sequence generated from analyzing the graph data of FIG. 4. To the left of the graphs are the bases associated with each molecular weight as indicated by the tag set definition table for set number 1. Since the graph for molecular weight 100 has a peak corresponding to positions 1, 4, and 7, the base stored in the sequence at positions 1, 4, and 7 are all A's. The display ODN sequence component then displays information in a format similar to FIG. 4. The user is then given an opportunity to correct any of the bases in the sequence that may be incorrect. Although the peak data is fairly discrete in the example of FIG. 4, it may be that in actual data the peaks may not be as readily identifiable. As a result, the peak detection algorithm may inadvertently detect a wrong peak. The display of the information of FIG. 4 allows the user to see graphically the peak information and the corresponding sequence and make corrections as necessary.

Figure 5:
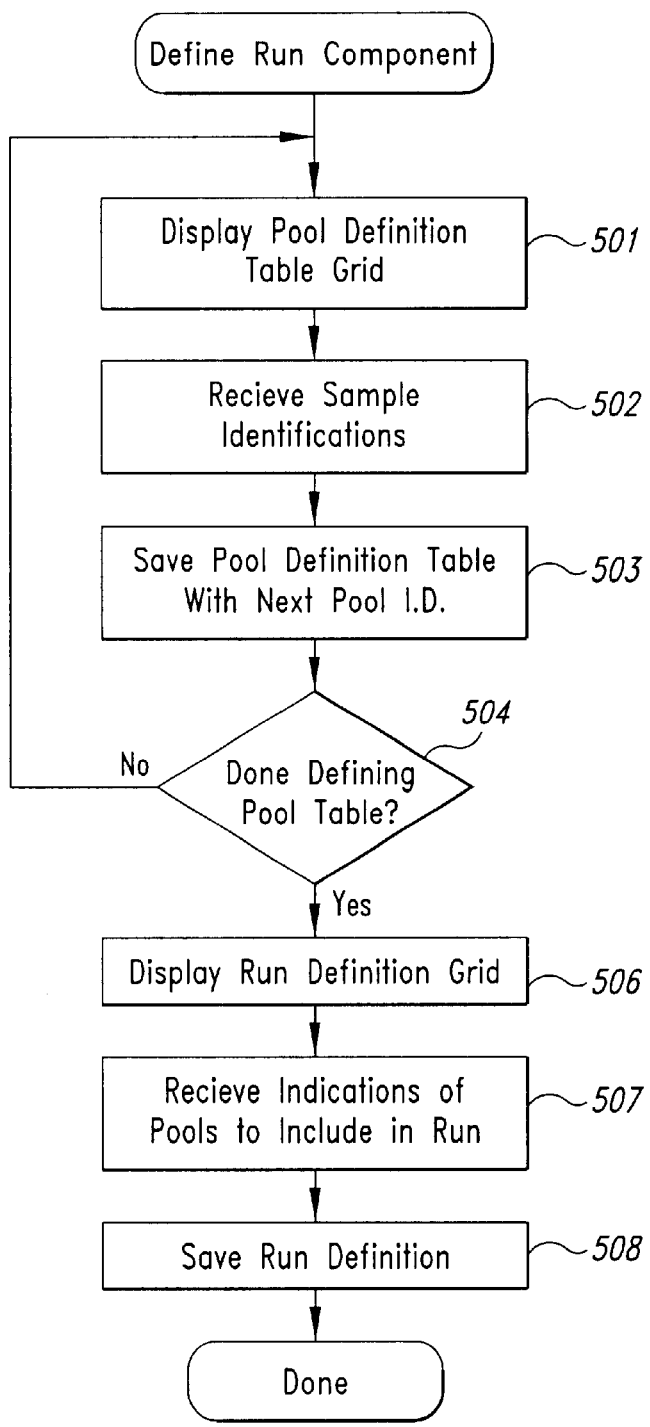
FIG. 5 is a flow diagram of a routine that implements the define run component.

FIG. 5 is a flow diagram of a routine that implements the define run component. The define run component allows a user to specify which tag sets are being used for which sample ODNs, which sample ODNs are being pooled together, and which pools of sample ODNs are to be run through the nucleotide sequencing system simultaneously. In steps 501–504, the routine loops allowing the user to specify the set of molecular tags assigned to each sample ODN that is assigned to each pool. In step 501, the routine displays a pool definition grid. The pool definition grid corresponds approximately to the outline of the pool definition table as shown in FIG. 2. The number of sets are predefined. The user inputs the sample identification (name of the person) for each sample ODN in the pool in the row corresponding to the molecular tag set assigned to that sample ODN. In step 502, the routine receives the sample identifications. In step 503, the routine saves the pool definition table with the next pool ID. In step 504, if the user indicates that the definition of the pools is complete, then the routine continues as step 506, else the routine loops to step 501 to input the next pool definition. In step 506, the routine displays a run definition grid. In one embodiment, the run definition grid has a row for each possible pool in the run and one column containing a pool number and a reference to the pool definition table defining the pool for that run. In step 507, the routine receives the indications of the pools to include in the run from the user. In step 508, the routine saves the run definition information in the run definition table and completes.

Figure 6:
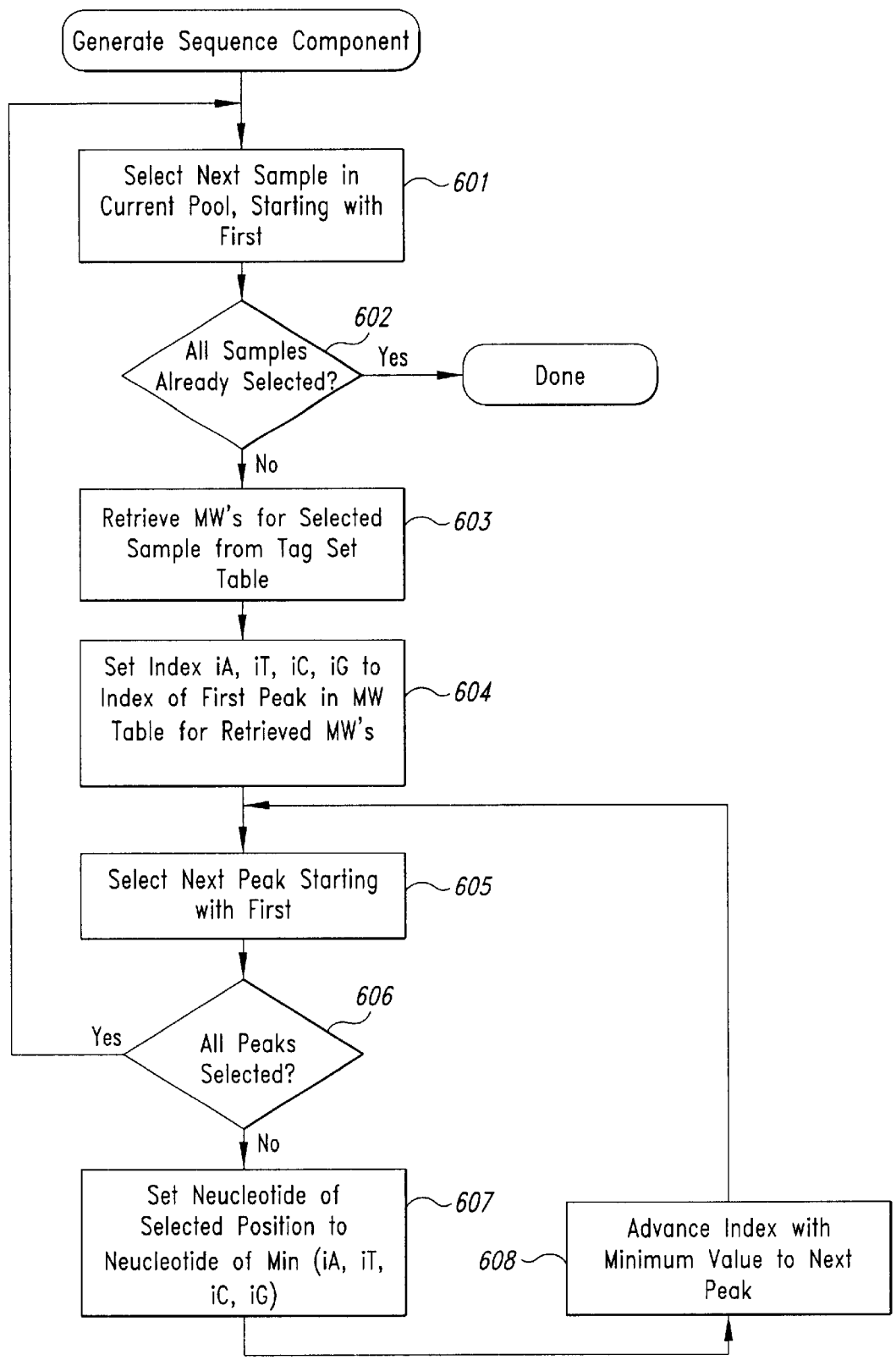
FIG. 6 is a flow diagram of a routine that implements the generate ODN sequence component.

FIG. 6 is a flow diagram of a routine that implements the generate ODN sequence component. This routine processes the data generated by the mass spectrometer for one pool. This routine is invoked for each pool that is processed in a run. In step 601–608, the routine loops selecting each sample in the pool and identifying each sequence for that sample. In step 601, the routine selects the next sample in the current pool starting with the first. In step 602, if all the samples have already been selected, then the routine is done, else the routine continues at step 603. In step 603, the routine retrieves the molecular weights for the selected sample from the tag set definition table. In step 604–608, the routine performs one iteration of the loop for each detected peak for the retrieved molecular weights. The loop identifies which of the retrieved molecular weights has a molecular weight peak that was next detected by the mass spectrometer. In step 604, the routine initializes indexes iA, iT, iC, and iG to the time of the first peak in the molecular weight table for each of the retrieved molecular weights. For example, for tag set number 1, the molecular weights are 100, 110, 120, and 130. Thus, referring to the graph of FIG. 4, the routine sets index iA equal to 2, index iT equal to 1, index iC equal to 4, and index iG equal to 3. These indexes are used to track the peaks in the molecular weight table. In step 605, the routine selects the next time starting with the first. In step 606, if all the molecular weight data for the retrieved molecular weights have already been selected, then the routine loops to step 601 to select the next sample, else the routine continues at step 607. In step 607, the routine sets the next base in the sequence to the base corresponding to the index with the minimum value. For example, the first time through the loop, the routine detects that index iT contains the minimum value which is 1. The routine then sets the first base in the sequence to T. In step 608, the routine advances the index with the minimum value to the time corresponding to its next peak. For example, during the first time through this loop, the routine then advances index iT to the time of its next peak which is at time 6. The routine then loops to step 605 to select the next peak.

Figure 7:
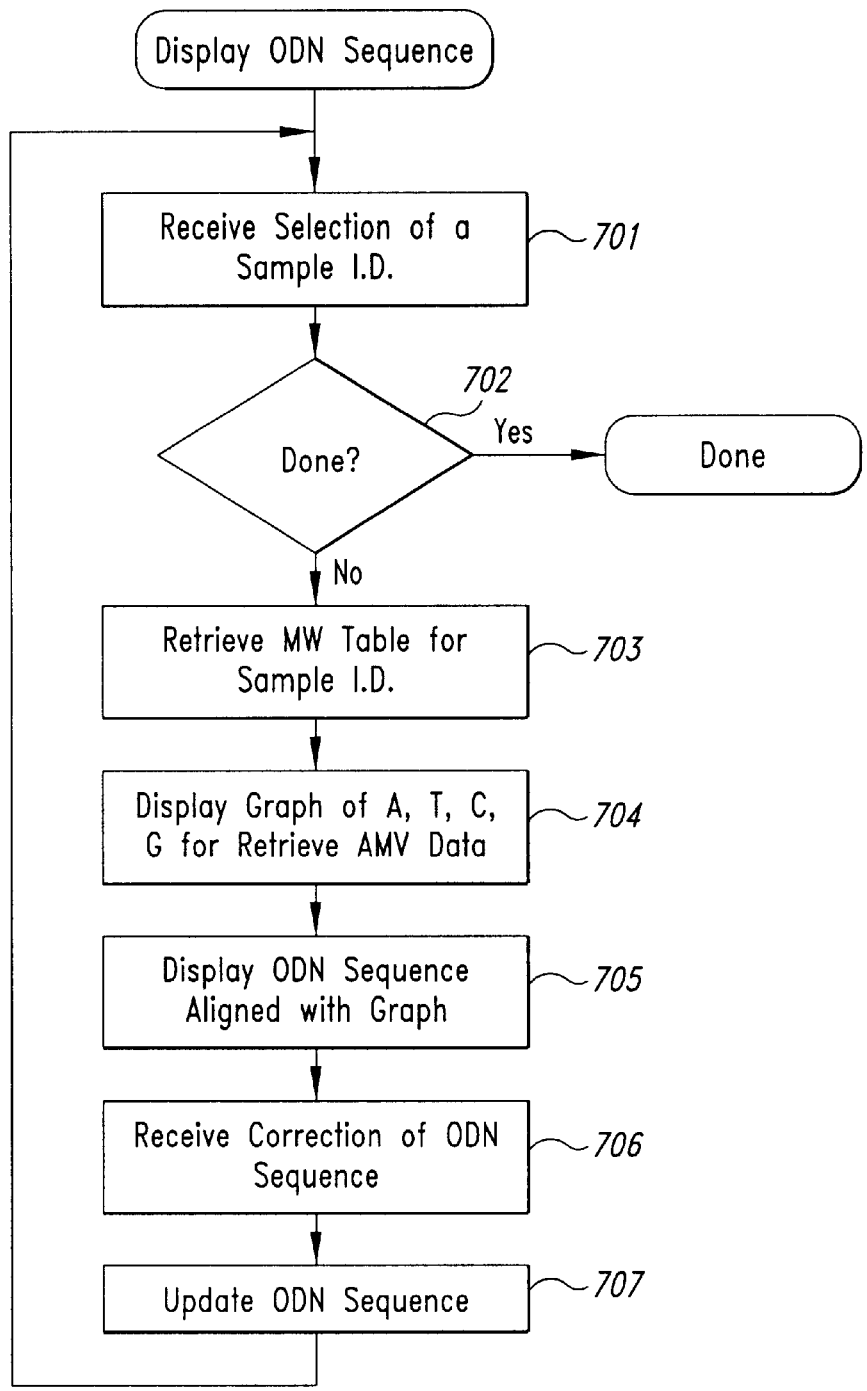
FIG. 7 is a flow diagram of a routine that implements the display ODN sequence component.

FIG. 7 is a flow diagram of a routine that implements the display ODN sequence component. In step 701, the routine receives the selection of a sample ID from a user. In step 702, if the user indicates that the display is complete, then the routine is done, else the routine continues at step 703. In step 703, the routine retrieves the portion of the molecular weight table that contains the information corresponding to the selected sample ID. The routine uses the pool definition table to determine the molecular tag set assigned to the selected sample ID. The routine then retrieves the molecular weights of that molecular tag set from the tag set definition table. In step 704, the routine displays a graph of assigned retrieved molecular weight data. FIG. 4 illustrates such a display of the graphs. In step 705, the routine displays the ODN sequence for the selected sample ID with the bases aligned underneath the peaks. In step 706, the routine allows the user to input a correction to any one of the bases in the displayed sequence. In step 707, the user changed the sequence, then the routine updates the ODN sequence and loops to step 701 to receive the next selection of the sample ID from the user.

Mutation Detection

Molecular tags with unique molecular weights can be also used to determine simultaneously whether multiple pairs of DNA (i.e., test DNA and reference DNA) have different sequences. The difference between each pair of DNA may be caused by a mutation of the DNA. Thus, the system to detect the difference is referred to as a mutation detection system. The mutation detection system uses the same configuration of the packed column, tag cleaving unit, and mass spectrometer as shown in FIG. 4 for the nucleotide sequencing. The BCID system contains additional components and tables to determine whether a mutation occurred for each of the multiple pairs of test and reference DNA.

The mutation detection system may process 48 pairs of DNA simultaneously. The first step of mutation detection is to place each pair of DNA samples to be compared into a pair of containers. Thus, there will be 48 pairs of containers in which one container of each pair contains the test DNA and the other container contains the reference DNA. The second step of mutation detection is to add two primers to each container. One primer will bind to one of the strands of DNA in each of the test and reference DNA, and the other primer will bind to the other strand of DNA in each of the test and reference DNA. One of the two primers in each pair of containers has a molecular tag weight but the molecular weight is different for each pair of containers. Each pair of containers is thus assigned a molecular tag with a unique molecular weight. The third step of mutation detection is to amplify the DNA. The fragment of DNA that is amplified is delimited by the binding sites for the two primers. The fourth step of mutation detection is to combine the test and reference DNA fragments of each pair of containers into a single container and then melt and re-anneal the contents of each container. When the melted strands are re-annealed, there is independent assortment of products, that is a fraction of the strands of the test DNA fragment will anneal to the complementary strand of the test DNA fragment, a fraction of the strands of the reference DNA fragment will anneal to the complementary strand of the reference DNA fragment, and, a fraction of the strands of the test DNA fragment will anneal to complementary strands of the reference DNA fragment to form a test-reference DNA fragment. If the test DNA fragment has a sequence that is different from the reference DNA fragment, then a mismatch of one or more of the bases will result. For example, the base T may be aligned with the base C or the base G. Because of this mismatch, the test-reference DNA fragments have a conformation that is different from either the test-test DNA fragments or the reference-reference DNA fragments. Of course, if the test and reference DNA fragments are the same, then the conformation of the test-reference DNA fragment is the same as that of the test-test or reference-reference DNA fragments.

The fifth step of mutation detection is to combine the contents of all the containers and elute the combined contents through the packed column. The various DNA fragments will travel through the packed column at different rates depending on their conformation. In particular, a test-reference DNA fragment will exit the packed column after the corresponding test-test and reference-reference DNA fragments if there is mismatching. The sixth step of mutation detection is to send the output of the packed column to the tag cleaving unit and to send the cleaved molecular tags to the mass spectrometer. The mass spectrometer records the molecular weights at various time intervals.

The output of the mass spectrometer includes for each time interval the number of molecular tags detected for each molecular weight. If there are two peaks for the same molecular weight at different times, then one peak represents the test-reference DNA fragments and the other peak represents the test-test and the reference-reference DNA fragments. The detection of two peaks indicates that the test-reference DNA fragments had a conformation different from the test-test and the reference-reference DNA fragments. Thus, the test DNA fragment and the reference DNA fragments have different sequences and a mutation is indicated.

The BCID system for mutation detection includes tables similar to those used in nucleotide sequence and analysis. The tag definition table contains a row for each of the 48 molecular tags with an indication of the corresponding molecular weights. The pool definition table contains a row for each of the 48 pairs of test and reference DNA fragments. Each row contains the identification of the pair (e.g., John Smith) and the identification of the molecular tag assigned to that pair. The BCID system processes the molecular weight table generated by the mass spectrometer to determine whether the pairs of the DNA are the same. The BCID system then loops selecting the rows of the pool definition table. The BCID system determines the molecular weight associated with the selected row from the tag definition table. The BCID system then analyzes the molecular weight table for that molecular weight to determine whether there were one or two peaks for that molecular weight. If there were two peaks, then the BCID system indicates that the DNA sequence of the test fragment is different from that of the reference fragment, that is, that there has been a mutation in the test fragment.

Differential Display

Molecular tags with unique molecular weights can also be used to determine simultaneously characteristics of a population of test mRNA when multiple primers are applied to the population of test mRNA. These characteristics can then be compared to the characteristics of a population of reference mRNA determined from the application of the same primers. The differences in the characteristics can be noted. The portion of the mRNA that results in the difference can be identified and sequenced using the nucleotide sequencing system. The process of identifying the differences is referred to as differential display analysis. The goal of differential display is to identify individual mRNA species present in one mRNA population and reduced or absent in the other. The differential display system of the present invention uses the same configuration of the packed column, tag cleaving unit, and mass spectrometer as shown in FIG. 4 for the nucleotide sequencing, with the addition of a flow splitter and fraction collection. The BCID system contains additional components and tables to identify differences between the population of test mRNA and the population of reference mRNA.

The differential display system simultaneously processes the results of applying multiple primers to the population of test mRNA. The first step of differential display is to produce test cDNA corresponding to the population of test mRNA. The second step is to add a portion of the cDNA into separate containers. The third step of differential display is to add a unique pair of primers, one of which has a unique molecular tag to each container. The primers in each container will bind to a fraction of the cDNA in the container. The fourth step is to amplify the contents of each container. The amplified contents will result in multiple fragments of cDNA synthesized starting at the binding sites of the primers. Thus, each primer pair will produce a set of fragments with different length and different sequences. This set is a subset of the cDNA population in the original sample. The fifth step of differential display is to combine the contents of all the containers and elute the combined contents through the packed column. Since the fragments will have different lengths, the fragments will elute through the packed column at different speeds. Thus, the contents of each container will elute as a series of peaks, each peak representing a fragment of a given length. Because the fragments in each container have a molecular tag with a unique molecular weight, the contents of each container can be uniquely identified by the mass spectrometer. The sixth step of differential display is to send the output of the packed column to the tag cleaving unit and to send the cleaved molecular tags to the mass spectrometer. The mass spectrometer records the molecular weights at various time intervals. The output of the mass spectrometer includes for each time interval the number of molecular tags for each detected molecular weight. Each peak in the time series for a single tag represents a fragment amplified from the original cDNA population. Thus, the presence or absence of a particular peak is correlated with the presence or absence of an individual mRNA in the mRNA population.

The BCID system for differential display includes tables similar to those used in nucleotide sequence analysis. The tag definition table contains a row for each of the molecular tags with an indication of the corresponding molecular weight. The pool definition table contains a row for each of the containers to identify the primer and identify the molecular tag applied to that primer. The BCID system compares the molecular weight table generated by the mass spectrometer for the population of test mRNA to the molecular weight table generated for the population of the reference mRNA that is processed in the same manner as the test mRNA. In particular, the BCID system selects the molecular weight assigned to each primer. The BCID system compares the molecular weight data for the test mRNA to the reference mRNA for the selected molecular weight and notes any significant differences. These difference indicate that a fragment of the test mRNA is different from the corresponding fragment of the reference mRNA.

The BCID system also allows these differences to be sequenced. The BCID system records the time associated with any of the noted differences between the test mRNA and the reference mRNA. The BCID system then requests that the user elute through the packed column additional contents of the container that was amplified with the molecular tag with the molecular weight for which the differences were noted. At the recorded time, the BCID system causes the shunt at the bottom of the packed column to direct the output of the packed column to a collection container, rather than the tag cleaving unit, for a short time period. The contents of the collection container are thus the fragments which resulted in the noted differences. These fragments can then be sequenced using the nucleotide sequencing system described above, or identified by other standard techniques.

Suitable biomolecules which are associated with tags of unique molecular weights according to the present invention are described in U.S. patent application Ser. Nos. 08/786,835; 08/786,834 and 08/787,521, each filed on Jan. 22, 1997, as well as in three U.S. continuation-in-part patent applications having application Ser. Nos. 08/898,180; 08/898,564; and 08/898,501, each filed Jul. 22, 1997; and in PCT International Publication Nos. WO 97/27331; WO 97/27325; and WO 97/27327. These six U.S. Patent Applications and three PCT International Publications are each hereby fully incorporated herein by reference in their entireties.

Biomolecule arrays which may be used in the methods of the present invention may be prepared as disclosed in U.S. patent application Ser. No. 09/120,386 titled "Polyethylenimine-Based Biomolecule Arrays" filed concurrently herewith, which claims the priority benefit of U.S. Provisional Patent Application No. 60/053,352 filed Jul. 22, 1997, as well as techniques described in U.S. patent application Ser. No. 09/120,689 titled "Apparatus and Methods For Arraying Solution Onto A Solid Support" filed concurrently herewith, which claims the priority benefit of U.S. Provisional Patent Application No. 60/053,435 filed Jul. 22, 1997, all being fully incorporated herein by reference in their entireties.

The methods of the present invention may also be applied to analyzing amplification and other enzymatic reactions, as described in U.S. patent application Ser. No. 09/120,689 titled "Amplification And Other Enzymatic Reactions Performed On Nucleic Acid Arrays" filed concurrently herewith, which claims the priority benefit of U.S. Provisional Patent Application No. 60/053,428 filed Jul. 22, 1997, as well as in arrays containing more than one oligonucleotide sequence within an element. Biomolecule arrays containing more than one oligonucleotide sequence within an element, and uses thereof, are described in U.S. patent application Ser. No. 09/785,105 titled "Multiple Functionalities Within An Array Element And Uses Thereof" filed concurrently herewith, which claims the priority benefit of U.S. Provisional Patent Application No. 60/053.436 filed Jul. 22, 1997. Each of these applications is fully incorporated herein by reference in their entirety.

Although the present invention has been described in terms of various embodiments, it is not intended that the invention be limited to these embodiments. Modifications within the spirit of the invention will be apparent to those skilled in the art per the scope of the present invention is defined by the claims which follow.

What is claimed is:

1. A method in a computer system for correlating known characteristics of nucleic acid molecules to molecular tags with unique molecular weights that have been associated with the nucleic acid molecules or portions thereof, the method comprising:

receiving an indication of a mapping of known characteristic(s) of each nucleic acid molecule to the corresponding molecular weight of the molecular tag associated with the known characteristic(s);

receiving an indication of the molecular weights detected when analyzing the tags that have been dissociated from the nucleic acid molecules or portions thereof, wherein the tags are separated based on a determined characteristic of the associated nucleic acid molecules or portions thereof other than the sequences of the nucleic acid molecules before the dissociation of the tag from the nucleic acid molecules or portions thereof; and for each molecular weight detected
determining based on the received mapping the known characteristic(s) of the nucleic acid molecule corresponding to the detected molecular weight; and
indicating that the nucleic acid molecule has the determined characteristic.

2. The method of claim 1 wherein the molecular tags are applied to primers used when synthesizing the nucleic acid molecules.

3. The method of claim 1 wherein the indicating further identifies a base sequence of a nucleic acid molecule.

4. The method of claim 1 wherein the known characteristic of a nucleic acid molecule identifies a primer and a base for synthesizing the nucleic acid molecule or a portion thereof, wherein the molecular weights are detected in an order corresponding to the positions of the bases in a base sequence of the nucleic acid molecule.

5. The method of claim 4 wherein the known characteristic further identifies one of multiple nucleic acid molecules which are analyzed simultaneously.

6. The method of claim 1 wherein the indicating further indicates whether one nucleic acid molecule is different from another nucleic acid molecule.

7. The method of claim 1 wherein the known characteristic identifies a primer for synthesizing a test nucleic acid molecule and a reference nucleic acid molecule, the resulting tagged test and reference nucleic acid molecules have been melted and re-annealed, and when the same molecular weight is detected at different times, the indicating indicates that the base sequences of the test nucleic acid molecule and the reference nucleic acid molecule are different.

8. The method of claim 1 wherein the indicating further identifies differences between two populations of mRNA.

9. The method of claim 1 wherein the nucleic acid molecules are cDNA molecules and the known characteristic identifies a primer that has been used to synthesize the cDNA molecules and wherein the number of peaks that the molecular tags with the same molecular weight are detected reflects the number of different cDNA molecules synthesized from the primer.

10. The method of claim 9 wherein the number of peaks a particular molecular tag detected in one population is compared to the number of peaks the same molecular tag is detected in another population of cDNA.

11. A method in a computer system for simultaneously determining the sequence of a plurality of sample oligonucleotides (ODNs), each sequence having four bases A, T, C, and G, the method comprising:

for each of the plurality of sample ODNs, receiving an indication of four molecular weights of molecular tags associated with the sample ODN, each of the four molecular weights corresponding to one of the four bases, each molecular weight being unique among all the molecular weights of all the molecular tags to be applied to all sample ODNs; and for each of a plurality of positions corresponding to a sequence length,
receiving an indication of the molecular weights of the molecular tags that have been associated with synthesized ODNs comprising base sequences identical to portions of the sample ODNs, the tags separated based on a characteristic of the associated synthesized ODNs other than the sequence of the associated synthesized ODNs and subsequently dissociated from the synthesized ODNs, the molecular weights being detected by a mass spectrometer, wherein the mass spectrometer detects one of the four molecular weights assigned to each of the plurality of sample ODNs for each position; and for each of the plurality of sample ODNs,
determining the base to which the detected molecular weight is assigned using the received indications for the sample ODN; and
setting the base at the position in the sequence for the sample ODN.

12. The method of claim 11 including
for each of the four bases, displaying a graph illustrating the detection of the molecular weights assigned to that base for the selected sample ODN; and
displaying the sequence for the sample ODN.

13. The method of claim 12 including receiving from a user a change to the displayed sequence.

14. A method in a computer system for determining whether a plurality of pairs of a test fragment and a reference fragment of DNA are different, the method comprising:

for each of the plurality of pairs of fragments, at various times, receiving an indication of the number of a molecular tag with a unique molecular weight that is associated with, but subsequently dissociated from, the pair of fragments, wherein the tags are separated based on a characteristic of the associated DNA fragments other than the sequences of the DNA fragments before the dissociation of the tag from the DNA fragments; and for each of the unique molecular weights of the molecular tags,
determining whether there is more than one peak in the number of molecular tags detected for that molecular weight; and
indicating that the pair of DNA fragments are different when it is determined that there is more than one peak in the number of molecular tags detected for that molecular weight.

15. A method in a computer system for identifying whether two populations of mRNA are different, the method comprising:

for each of a plurality of primers, at various times, receiving an indication of the number of a molecular tag with a unique molecular weight, the molecular tag being associated with the cDNA derived from the mRNA using each of the primers, separated based on a characteristic of the cDNA other than the sequence of the cDNA, and subsequently dissociated from the cDNA; and for each of the unique molecular weights of molecular tags,
- comparing the presence of a peak in the number of molecular tags detected for that molecular weight at any particular time derived from one population of mRNA with that of the other population; and
- indicating that the two populations of mRNA are different when there is a difference in the presence of the peak.

16. A computer system for correlating known characteristics of nucleic acid molecules to molecular tags with unique molecular weights that have been associated with the nucleic acid molecules or portions thereof, comprising:

a molecular tag definition table indicating the molecular weight of each molecular tag;

a defined run component for generating a mapping of each nucleic acid molecule to a molecular tag;

a molecular weight collection component for receiving an indication of the molecular weights of the molecular tags that have been associated with the nucleic acid molecules or portions thereof, separated based on a determined characteristic of the associated nucleic acid molecules or portions thereof other than the sequences of the nucleic acid molecules, and subsequently dissociated from the nucleic acid molecules or portions thereof; and a correlation component that determines, based on the received mapping, the known characteristic of the nucleic acid molecule corresponding to the detected molecular weight, and indicates that the nucleic acid molecule has the determined characteristic.

17. The computer system of claim 16 wherein the correlation component further indicates the base sequences of the nucleic acid molecules.

18. The computer system of claim 16 wherein the correlation component further indicates whether one nucleic acid molecule is different from another nucleic acid molecule.

19. The computer system of claim 16 wherein the correlation component further identifies differences between two populations of mRNA.

* * * * *